United States Patent [19]
Eckert et al.

[11] Patent Number: 5,858,556
[45] Date of Patent: Jan. 12, 1999

[54] MULTILAYER COMPOSITE TUBULAR STRUCTURE AND METHOD OF MAKING

[75] Inventors: John K. Eckert, Boyertown; Jeffrey M. Farina, Zionsville, both of Pa.; Joseph P. Gadda, Brick Township, N.J.; Jeffrey C. Kelly, Wilmington, Del.; John G. Thomas, Berwyn, Pa.

[73] Assignee: UTI Corporation, Collegeville, Pa.

[21] Appl. No.: 784,622

[22] Filed: Jan. 21, 1997

[51] Int. Cl.$^6$ ................................. A61F 2/06; C21D 9/08
[52] U.S. Cl. ........................... 428/586; 428/662; 428/670; 428/672; 428/685; 148/521; 606/195; 623/1; 623/12; 228/127; 228/194
[58] Field of Search .................................. 428/586, 685, 428/660, 661, 662, 670, 672; 148/521; 606/194, 195; 623/1, 12; 138/143; 228/194, 195, 193, 127

[56] References Cited

U.S. PATENT DOCUMENTS

| | | | |
|---|---|---|---|
| 2,836,181 | 5/1958 | Tapp | 128/334 |
| 3,155,095 | 11/1964 | Brown | 128/334 |
| 3,562,820 | 2/1971 | Braun | 3/1 |
| 3,585,647 | 6/1971 | Gajewski et al. | 3/1 |
| 4,542,539 | 9/1985 | Rowe, Jr. et al. | 623/16 |
| 4,553,545 | 11/1985 | Maass et al. | 128/341 |
| 4,731,073 | 3/1988 | Robinson | 623/1 |
| 4,733,665 | 3/1988 | Palmaz | 128/343 |
| 4,739,762 | 4/1988 | Palmaz | 128/343 |
| 4,760,849 | 8/1988 | Kropf | 128/341 |
| 4,776,337 | 10/1988 | Palmaz | 128/343 |
| 4,793,348 | 12/1988 | Palmaz | 128/325 |
| 4,834,755 | 5/1989 | Silvestrini et al. | 623/13 |
| 4,878,906 | 11/1989 | Lindemann et al. | 623/1 |
| 4,917,666 | 4/1990 | Solar et al. | 604/95 |
| 4,981,478 | 1/1991 | Evard et al. | 604/282 |
| 4,994,069 | 2/1991 | Ritchart et al. | 606/191 |
| 4,994,071 | 2/1991 | MacGregor | 606/194 |
| 5,037,427 | 8/1991 | Harada et al. | 606/108 |
| 5,059,211 | 10/1991 | Stack et al. | 606/198 |
| 5,071,407 | 12/1991 | Termin et al. | 604/104 |
| 5,163,958 | 11/1992 | Pinchuk | 623/11 |
| 5,192,307 | 3/1993 | Wall | 623/1 |
| 5,197,978 | 3/1993 | Hess | 623/1 |
| 5,234,457 | 8/1993 | Andersen | 606/198 |
| 5,282,823 | 2/1994 | Schwartz et al. | 606/198 |
| 5,304,120 | 4/1994 | Crandell et al. | 604/52 |
| 5,306,286 | 4/1994 | Stack et al. | 606/198 |
| 5,316,023 | 5/1994 | Palmaz et al. | 128/898 |
| 5,342,348 | 8/1994 | Kaplan | 604/891 |
| 5,356,433 | 10/1994 | Rowland et al. | 623/11 |
| 5,372,600 | 12/1994 | Beyar et al. | 606/108 |
| 5,419,760 | 5/1995 | Narciso, Jr. | 604/8 |
| 5,423,849 | 6/1995 | Engelson et al. | 606/191 |
| 5,423,885 | 6/1995 | Williams | 623/1 |
| 5,425,739 | 6/1995 | Jessen | 606/155 |

(List continued on next page.)

OTHER PUBLICATIONS

The Palmaz Balloon–Expandable Stent, by Johnson & Johnson Interventional Systems Co., no date.

*Primary Examiner*—John J. Zimmerman
*Attorney, Agent, or Firm*—Seidel, Gonda, Lavorgna & Monaco, PC

[57] ABSTRACT

A multilayer composite tubular structure for use as a stent in surgical procedures has an outer layer of biocompatible material, a middle layer of radiopaque material, and an inner layer of biocompatible material. The layers are metallurgically bonded, to form a composite stent which is ductile and permits large deformation without delamination between the biocompatible and radiopaque layers. The composite structure formed is visible on a fluoroscope, yet does not obstruct the details of the stent itself, or of the anatomical features surrounding the stent.

A process of forming a multilayer composite tubular structure is also disclosed. A tube formed from radiopaque material is coaxially surrounded by a tube of biocompatible material. The tubes are simultaneously reduced, such as by tube drawing, swaging, or deep drawing, until a composite structure of a desirable diameter and wall thickness is formed. The tubes are then heat treated to cause diffusion bonding of the biocompatible and radiopaque layers.

57 Claims, 7 Drawing Sheets

U.S. PATENT DOCUMENTS

| | | | |
|---|---|---|---|
| 5,441,516 | 8/1995 | Wang et al. | 606/198 |
| 5,443,496 | 8/1995 | Schwartz et al. | 623/1 |
| 5,443,498 | 8/1995 | Fontaine | 623/1 |
| 5,449,373 | 9/1995 | Pinchasik et al. | 606/198 |
| 5,476,508 | 12/1995 | Amstrup | 623/1 |
| 5,480,423 | 1/1996 | Ravenscroft et al. | 623/1 |
| 5,503,636 | 4/1996 | Schmitt et al. | 606/200 |
| 5,507,767 | 4/1996 | Maeda et al. | 606/198 |
| 5,514,154 | 5/1996 | Lau et al. | 606/195 |
| 5,522,822 | 6/1996 | Phelps et al. | 606/151 |
| 5,527,354 | 6/1996 | Fontaine et al. | 623/1 |
| 5,536,274 | 7/1996 | Neuss | 623/1 |
| 5,540,701 | 7/1996 | Sharkey et al. | 606/153 |
| 5,545,210 | 8/1996 | Hess et al. | 623/1 |
| 5,551,444 | 9/1996 | Einlayson | 128/772 |
| 5,628,787 | 5/1997 | Mayer | 623/1 |
| 5,630,840 | 5/1997 | Mayer | 623/1 |
| 5,637,113 | 6/1997 | Tartaglia et al. | 623/1 |
| 5,662,713 | 9/1997 | Anderson et al. | 623/12 |
| 5,667,523 | 9/1997 | Bynon et al. | 606/198 |
| 5,679,470 | 10/1997 | Mayer | 428/662 |

MULTILAYER COMPOSITE TUBULAR STRUCTURE AND METHOD OF MAKING

FIELD OF THE INVENTION

The present invention relates to the field of multilayer composite tubes and, in particular, stents for use in surgical procedures. The present invention provides a multilayer composite tubular structure for use as a surgical stent which is visible on a fluoroscope, yet does not mask anatomical structures. The present invention also provides a multilayer stent which does not delaminate upon deployment and expansion.

BACKGROUND OF THE INVENTION

Stents are utilized in a wide range of surgical procedures. For example, stents are used to repair and support injured tissue during the subsequent healing process. The stent is delivered to the target site and expanded to several times its original diameter until the stent contacts the surrounding tissue. This process is known as initial expansion of the stent. Next, the stent is further expanded to imbed the stent into the walls of the surrounding anatomical structure, for example, an artery. This process is known as imbedding. The process of initial expansion and imbedding is known as deployment. Once the stent is expanded, it takes on a permanent set.

An example of a common surgical procedure involving the use of a stent is the placement of a stent within a coronary artery after removal of plaque from within the artery. In that case, the stent is used to support the vessel which has been blocked by atherosclerotic plaque.

Stents are also used in surgical procedures involving the ureters or the urethra. For example, in prostate surgery, stents are used to hold open tracts of the urinary system.

The placement and positioning of the stent is crucial during all surgical procedures such as those described above. Thus, various procedures have been developed which allow a physician or surgeon to view a stent in situ for proper placement. The most common of these procedures is to view the stent using a fluoroscope.

Prior art stents are commonly made of a single material such as stainless steel, tantalum, or Nitinol™, with the most common material used being stainless steel. A major disadvantage of a stainless steel stent is that it is transparent to a fluoroscope. Therefore, using a stainless steel stent requires that opaque dyes be injected in the bloodstream to make the stent visible to the surgeon for positioning and deployment. These dyes dissipate very quickly, making the stent visible for only a brief period of time. Thus, procedures involving stainless steel stents and the use of dye to view the stent require rapid placement and deployment of the stent. Additionally, the lack of visibility of the stent makes it extremely difficult, if not impossible, to verify that the stent has not changed location over time.

Tantalum is a radiopaque material widely used in stents. A solid tantalum stent must have a minimum thickness to be useful in deployment and function. The required thickness of the solid tantalum stent results in a high luminosity on a fluoroscope, and in turn causes several problems. One is that the fluoroscope image produced by tantalum stents is so luminous that it obliterates the detail of the stent pattern and the detail at the stent/vessel interface. Because it is impossible to view the stent/vessel interface, accurate placement of the stent at vessel bifurcations is tedious. Moreover, the fact that the stent structure cannot be accurately observed makes more difficult the determination of whether vascular conditions, such as restenosis, have occurred at the stent site.

Because stents are used at various anatomical sites, it is necessary to vary the thickness, and therefore the strength of the stent, to compensate for anatomical variations. For example, stents may be used at anatomical sites having varying degrees of muscle mass. A multilayer stent would have to be able to compensate for variations in muscle mass, for example, with different thicknesses of the stent layers. Additionally, it would also be desirable to be able to vary the luminosity of a stent to compensate for different anatomical variations and varying degrees of muscle mass.

Surgical stents undergo tremendous plastic deformation during deployment. In a multilayer stent, the layers of the stent must not delaminate or separate. Any delamination of a multilayer stent could expose rough or jagged edges, leading to thrombosis, and direct anatomical injury, including the tearing of vessels.

It is a usual surgical practice to deploy, expand, and imbed surgical stents by means of a balloon unit. The use of these balloon units is well known in the stent art. The pressure employed to expand a surgical stent using a ballon unit is critical. Stents that require a higher pressure to expand run an increased risk of balloon rupture, which could lead to an embolism.

There is, therefore, a need for a stent which is visible on a fluoroscope, but does not mask anatomical structures.

There is also a need for a multilayer stent which can expand without delaminating.

There is also a need for a multilayer stent whose strength can be varied by varying its thickness to accommodate different anatomical structures.

There is further a need for a multilayer stent where its luminosity on a fluoroscope can be varied by changing the thickness of the layers of the stent to accommodate different anatomical structures.

There is still further the need for a multilayer stent where the stent is expanded at a lower pressure and which provides a decreased risk of balloon rupture upon deployment.

SUMMARY OF THE INVENTION

The present invention is directed to a structure that satisfies the need for a stent which is both visible on a fluoroscope, yet does not obstruct the details of the stent itself or the anatomical structures surrounding the stent. The present invention provides a truly innovative and effective solution to these needs.

A structure having features of the present invention comprises a multilayer composite stent. One layer of the stent is formed from a radiopaque material. Another layer of the stent is formed from a biocompatible material. The combination of these layers produces a structure which is both biocompatible and visible on a fluoroscope, yet does not mask the stent structure or the surrounding anatomical structure.

The present invention also provides for a method of making a multilayer composite structure having properties of the stent described above. A multilayer composite structure which is the subject of the present invention is created by reducing, such as by tube drawing, swaging, or deep drawing multiple tubes or strip as a composite and applying heat treatment to cause diffusion bonding of the layers. This results in a ductile structure that permits large deformation without delamination between the biocompatible and radiopaque layers.

DESCRIPTION OF THE DRAWINGS

For the purpose of illustrating the invention, there is shown in the drawings a form which is presently preferred; it being understood, however, that this invention is not limited to the precise arrangements and instrumentalities shown.

DETAILED DESCRIPTION OF THE INVENTION

Figure 1:
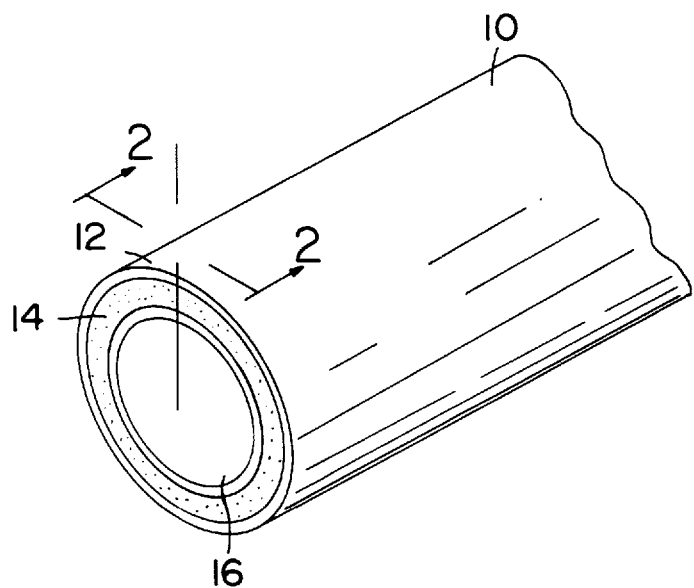
FIG. 1 shows a partial perspective view of a stent according to the present invention, before etching or machining.
Figure 2:
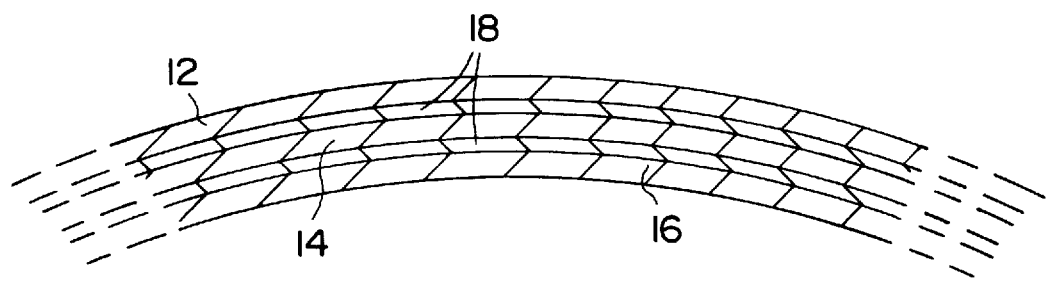
FIG. 2 shows a cross sectional view taken along line 2—2 in FIG. 1, showing the layers of the stent.

Referring now to the drawings, wherein like numerals indicate like elements, there is shown in FIGS. 1 and 2 a stent 10 in accordance with the present invention. In the preferred embodiment of the present invention shown in FIGS. 1, 2, and 3, a stent 10 comprises a multilayer composite tubular structure having an outer layer 12 of biocompatible material, a middle layer 14 of radiopaque material, and an inner layer 16 also of biocompatible material. In the preferred embodiment, the biocompatible material used for the outer layer 12 and inner layer 16 is stainless steel, while the radiopaque middle layer 14 is tantalum. These layers are bonded together using processes described below. The stent 10 illustrated in FIG. 3 has been etched and machined to produce a particular pattern.

It is recognized that other biocompatible materials can be substituted for stainless steel. It is also recognized that the radiopaque layer 14 is not limited to tantalum, and other materials, including but not limited to gold, platinum, and alloys of those materials, may be used without departing from the present invention.

In a stainless-tantalum-stainless stent such as stent 10, the tantalum layer 14 must have sufficient thickness to provide a sharp and clear image on a fluoroscope (not pictured). The thickness of the radiopaque tantalum layer 14 can be varied to provide the optimum luminescence for applications where the stent is delivered to vessels close to the surface, where low luminescence is required, or procedures deeper within tissue such as muscle, where a higher luminescence, and thus a thicker radiopaque tantalum layer 14, is required. The thickness of the radiopaque tantalum layer 14 can also be varied to accommodate for anatomical sites having tissue density variations, as these locations require different stent luminescence.

Figure 4:
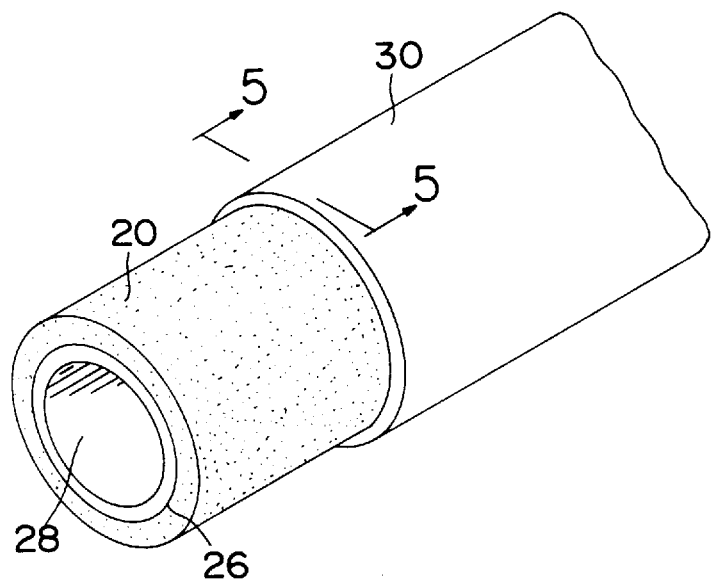
FIG. 4 shows a fragmentary partial cutaway view of a stent according to another embodiment of the present invention, before etching or machining.
Figure 5:
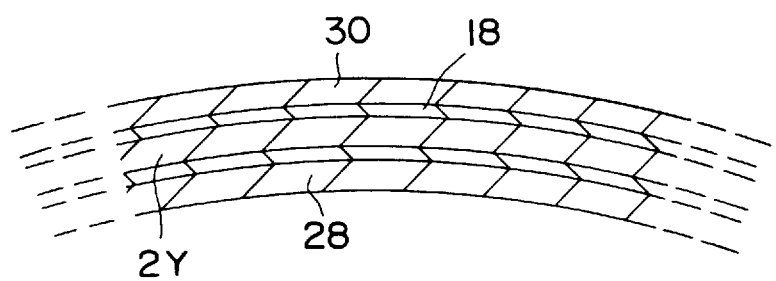
FIG. 5 shows a cross sectional view taken along line 5—5 in FIG. 4, showing the layers of the stent.

In another embodiment of the present invention, as shown in FIGS. 4 and 5, thin radiopaque layers 24 can be deposited on the outer surface 26 of a first tube 28 of biocompatible material through electroplating, or through vapor, chemical, or other film deposition techniques. In FIGS. 4 and 5, the relative thickness of the radiopaque layer 24 is exaggerated for clarity. The coated first tube 28 is then metallurgically bonded to a second tube 30, forming a diffusion layer 18, described below, between the radiopaque layer 24 and the second tube 30. In another embodiment, the radiopaque layer 24 is deposited on the inner surface of a first tube (not shown), which is then placed coaxially around and metallurgically bonded to a second tube.

The radiopaque layer 14 or 24 can therefore be from 1% to 95% of the wall thickness of the stent 10. Thus, the luminosity can be varied widely to accommodate for different tissue variations.

It is contemplated that additional layers can be added to the stent of the present invention to form stents of various compositions. For example, a five layer stent could be formed, having alternating layers of stainless steel and tantalum, with the stainless steel layers being the outer-most and inner-most layers.

Due to the large plastic deformation of the stent 10 which must occur during deployment and expansion, as previously described, the bond formed between the stainless steel and tantalum layers is critical to the proper function of the structure. A mechanical bond is not adequate to meet the requirements of stents according to of the present invention. Instead, a metallurgical bond, where diffusion of the material elements takes place, is the desired approach. This metallurgical bond is formed through the application of pressure and heat to the materials, as described below.

As illustrated in FIG. 2, concurrent with the formation of a metallurgical bond between the layers of the structure, a diffusion layer 18 is also created at the interface between adjacent layers 12 and 14, or 14 and 16. The characteristics of these diffusion layers 18 can be significantly affected and controlled by the proper heat treatment cycle, resulting in either a desired ductile diffusion layer 18, or an undesirable brittle intermetallic layer.

Heat treatment, temperature, and time relationships control the rates of transfer of the diffusing elements, resulting in diffusion layers 18 of different elemental composition and thickness. Heat treatment cycles must be optimized for different material combinations, so that the diffusion layer 18 maintains the ductility necessary for deployment. The diffusion layer 18 must also be of minimal thickness necessary to ensure bond integrity and ductility to prevent delamination during stent 10 expansion upon employment.

Figure 6:
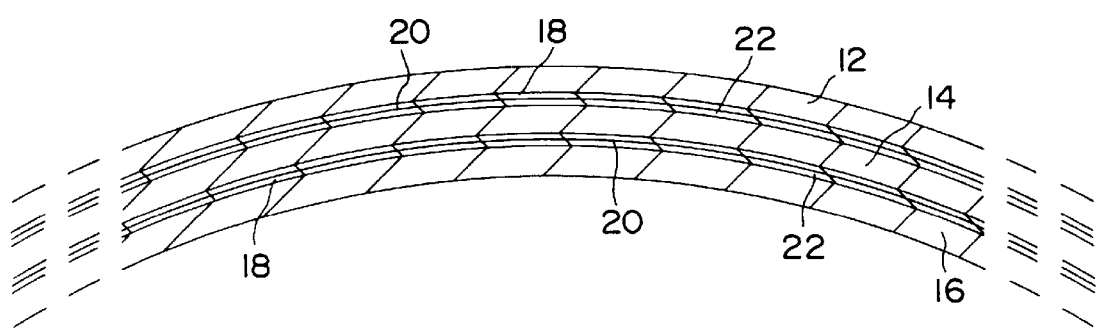
FIG. 6 shows a cross sectional view of another embodiment of a stent according to the present invention, showing a metallic interleaf between layers.

In another embodiment of the present invention, as shown in FIG. 6, the bonding together of materials which may not be readily compatible, and which would result in an undesirable brittle intermetallic layer being formed, can be accomplished through the use of a metallic interleaf 20. This interleaf 20 acts to control both the diffusion rate and the elements which are transported across the diffusion region 22. For example, a gold interleaf can be used to facilitate the formation of a proper diffusion layer 18.

A multilayer composite tubular structure having features of the present invention can be formed using the following processes.

EXAMPLE #1

Figure 3:
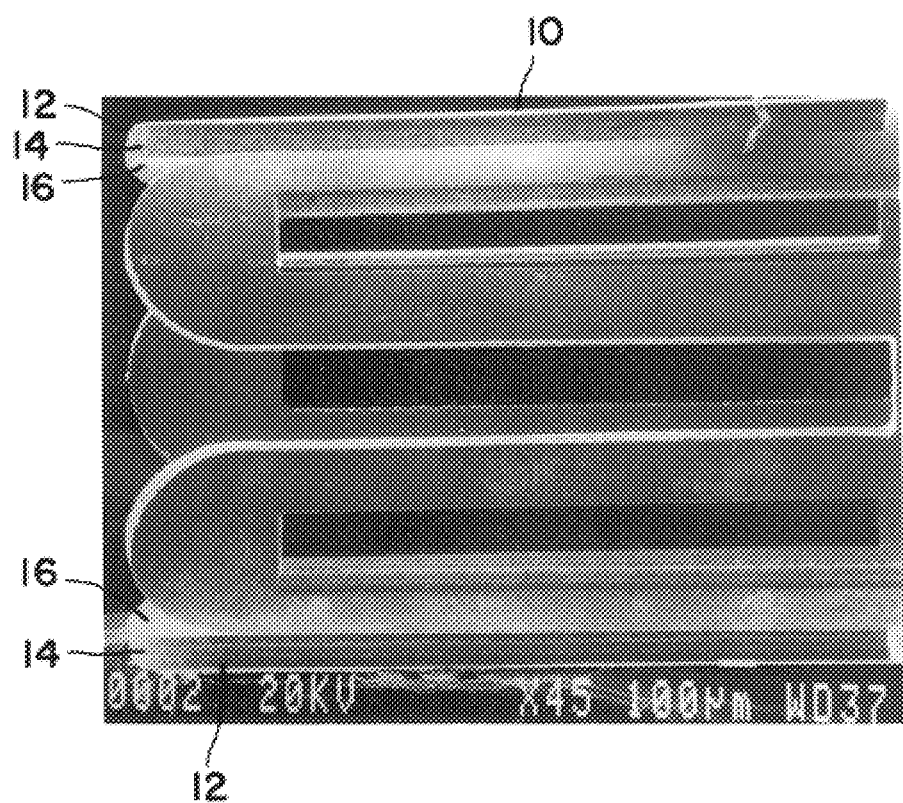
FIG. 3 is an electron micrograph of a portion of an actual stent in accordance with the present invention, after etching or machining.

As previously noted, the diffusion layer 18 between the stainless steel and tantalum is developed and controlled by the proper application of pressure and thermal treatment. This is well known in the art of diffusion bonding. In one example of a process that may be used in forming the present invention, an outer tube made of a biocompatible material, a middle tube made of radio-opaque material, and an inner tube made of a biocompatible, are arranged coaxially, and reduced simultaneously, such as by swaging or tube drawing, for example. The process of tube reduction in this fashion is well known in the art. An example of a composite tubular structure arranged in this manner is depicted in FIGS. 1 and 3.

In the multilayer composite tubular structure according to the invention, pressure at the interface between layers is developed as a result of the residual radial clamping stresses left in the tube after the composite drawing operation. Those skilled in the art of tube drawing will recognize that increasing the area reduction and varying the percentage of area reduction versus wall reduction will either increase or decrease the magnitude of this residual stress within certain limits.

In one example of this process, an outer tube of stainless steel, a middle tube of tantalum, and an inner tube of stainless steel, are arranged as described above to form the composite structure. To facilitate proper bonding between the layers, a residual clamping stress of at least 50 p.s.i. at the interface should be developed. In addition, annealing of the composite tube must be done within a limited range of time and temperatures. The lower limit of this time and temperature range should be at least 1550° F. for at least six minutes. The upper limit should be not greater than 1850° F. for a period no greater than 15 minutes. Annealing of the composite tube within these temperature ranges will provide a diffusion layer 18 of minimal thickness and elemental composition to maintain the required ductility to permit deployment and expansion at lower pressures, and still prevent delamination during expansion.

EXAMPLE #2

In another process of forming the present invention, a radiopaque material layer is deposited on the outer surface of an inner tube of biocompatible material. This arrangement is shown in FIG. 4. The radiopaque material may deposited through a cladding process such as vapor deposition, electroplating, spraying, or similar processes. An outer tube of biocompatible material is then placed around the clad inner tube.

The composite tubes are then drawn together and progressively reduced until the desired residual clamping stress is attained, as described above. The tubes are then heat treated as described above, forming a diffusion bond between the radiopaque layer and the inner surface of the outer tube.

It is recognized that this same process can be accomplished by depositing the radiopaque layer on the inner surface of the outer tube, and bonding that combination to the outer surface of the inner tube.

EXAMPLE #3

Another process which can be used to form a multiple composite tubular structure involves the use of a metallic interleaf 20. This is illustrated in FIG. 6. The interleaf 20 is placed between the biocompatible and radio-opaque layers, and acts to control the diffusion rate and/or the diffusing atoms which are transported across the diffusion region. The multiple tubes are then drawn together and progressively reduced until the desired residual clamping stress is attained, as described above. The tubes are then heat treated as described above, forming a diffusion bond between the radiopaque material and the biocompatible materials, which is facilitated by the interleaf 20.

EXAMPLE #4

Yet another process which can be used to form a multiple composite tubular structure according to the present invention involves the use of deep drawing from a multilayer strip 42. The process of deep drawing is well known in the art of tube formation.

Figure 7:
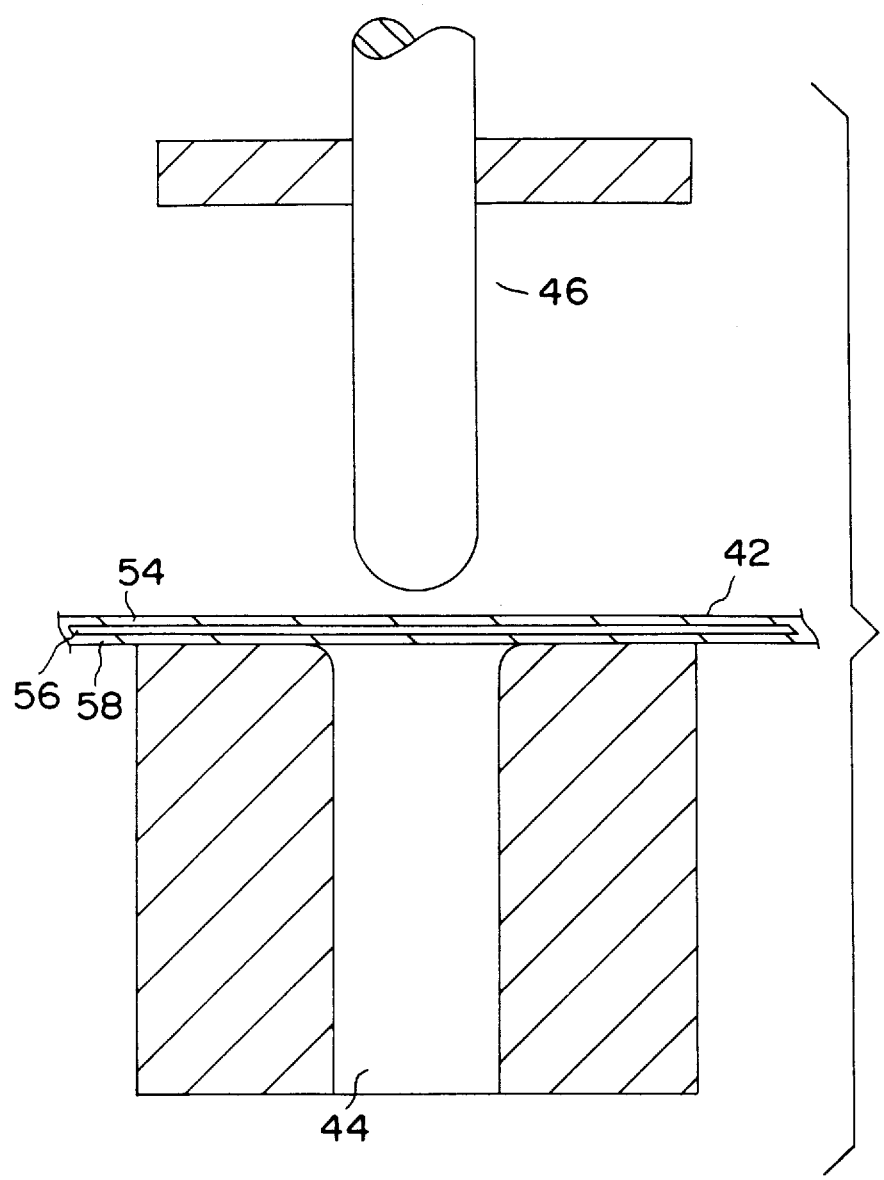
FIGS. 7–9 show a partially cross sectional view of one process of making a stent according to the present invention.
Figure 8:
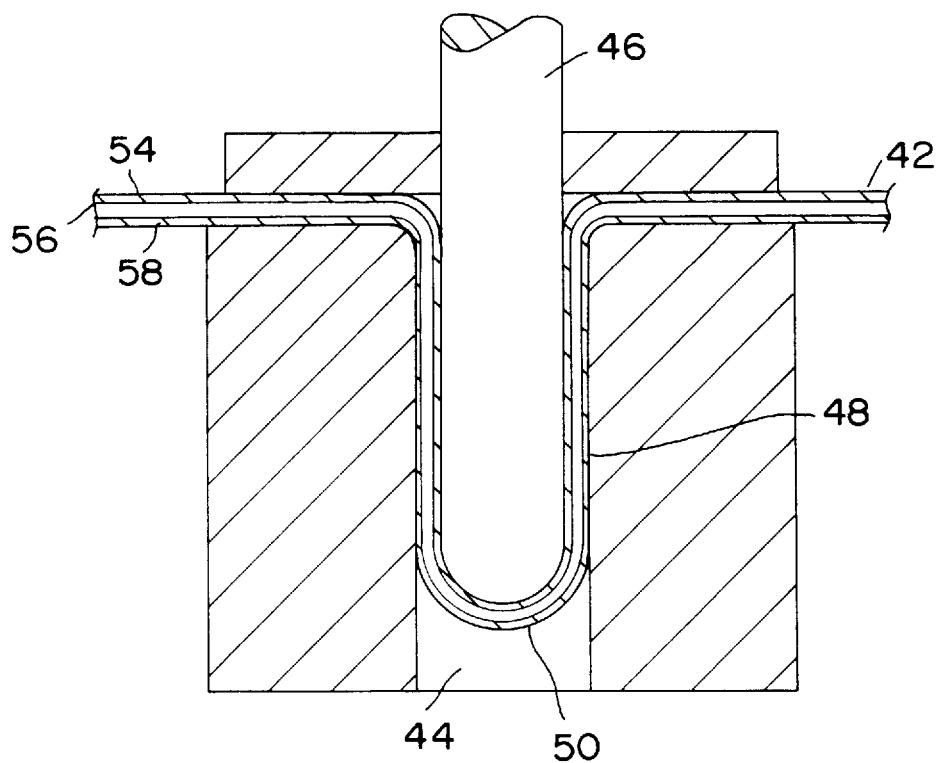
Figure 9:
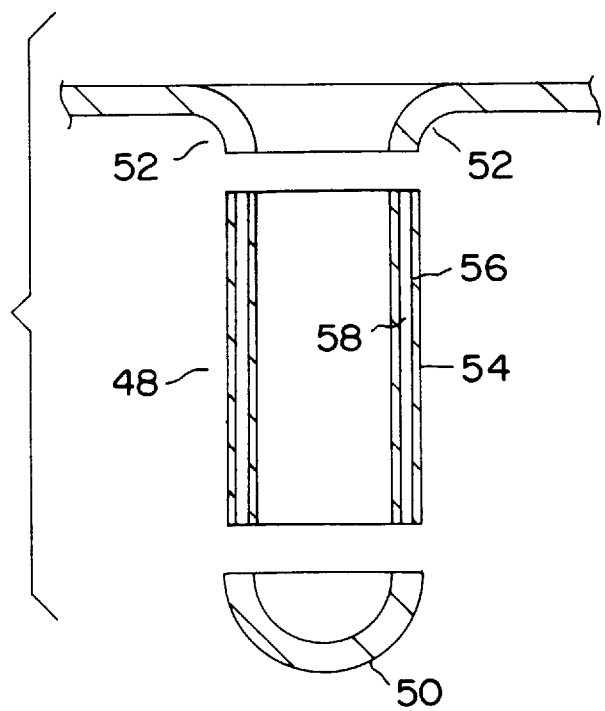

In one embodiment, as shown in FIGS. 7, 8, and 9, the multilayer strip 42 has a top layer 54 of stainless steel, a middle layer 56 of radiopaque material, and a bottom layer 58 of stainless steel. This strip 42 is prepared by metallurgically bonding the layers prior to the deep drawing process. In the course of the deep drawing process, as shown in FIG. 8, the strip 42 is placed over a die 44, and the strip 42 is forced into the die 44, such as by a punch 46. A tube 48 having a closed end 50 of a certain wall thickness is formed in the die 44. This process is repeated using a series of dies of progressively decreasing diameter until a multilayer tube 48 is formed having the desired diameter and wall thickness. For certain material combinations, it may be necessary to perform intermediate heat treatments, as described above, between the progressive drawing operations. Once a tube of desired thickness and dimensions has been formed, the closed end 50 and the curved edges 52 of the tube 48 are cut off, as illustrated in FIG. 9. Then, the tube is heat treated as described above until the proper intermetallic bond is formed between the layers.

An advantage of the composite structure described herein is that, for a wide range of radiopaque layer thickness and materials, the stent 10 can be expanded at a lower applied force, which translates into lower deployment pressures than those required for a solid stainless stent of the same wall thickness. This is due to the lower modulus of the composite structure. The lower modulus is caused by the lower yield strength of the radiopaque material and/or a contribution from a lower strain hardening coefficient.

Figure 10:
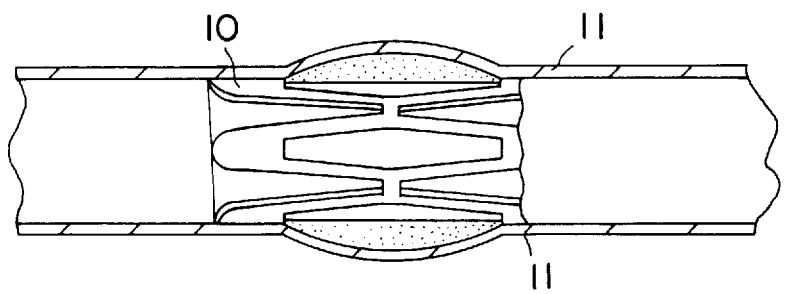
FIG. 10 shows a cross sectional view of a stent according to the present invention the present invention in place in an artery.
Figure 11:
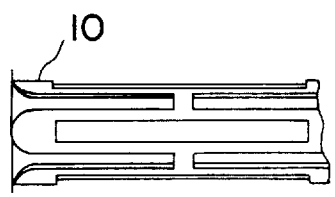
FIG. 11 shows a side view of a stent according to the present invention prior to expansion.

In a typical surgical procedure using a stent, the stent is initially expanded with a low pressure balloon (not shown) until the stent walls contact a vessel to be held open, for example, the walls of an artery. A stent 10 is illustrated in FIG. 10 contacting the walls of an artery 11. The low pressure balloon is then withdrawn, a high pressure balloon (not shown) is inserted, and the stent 10 is further expanded by the high pressure balloon into the artery wall 11. This second expansion is referred to as imbedding. The expansion and imbedding pressures of a composite stent having a 1:1:1 ratio of stainless steel:tantalum:stainless steel, as compared to a common stainless steel stent of the same thickness, are detailed in Table I below:

TABLE I

|  | Stainless steel | Multilayer Composite 1:1:1 (stainless:tantalum:stainless) |
|---|---|---|
| Deployment | 4 Atmospheres | 3.5 Atmospheres |
| Expansion (Imbedding) | 8 Atmospheres | 7 Atmospheres |

The ability to use lower expansion and imbedding pressures for the composite stent, as compared to the solid stainless steel stent, affects its safety and reliability. Because less pressure is needed to expand and imbed the composite stent of the present invention, there is less risk of tearing or otherwise injuring surrounding anatomical features, tissues, or vessels. Moreover, a lower stress is exerted on the balloon unit, thus decreasing the risk of balloon rupture and the concomitant risk of an embolism.

The present invention may be embodied in other specific forms without departing from the spirit or essential attributes thereof and, accordingly, reference should be made to the appended claims, rather than to the foregoing specification, as indicating the scope of the invention.

What is claimed is:

1. A multilayer composite tubular structure for use as a stent in surgical procedures, comprising:
   (a) an outer layer comprising a biocompatible material;
   (b) a middle layer comprising a radiopaque material metallurgically bonded to the outer layer; and
   (c) an inner layer comprising a biocompatible material metallurgically bonded to the middle layer.

2. The multilayer composite tubular structure according to claim 1, wherein the outer layer is stainless steel.

3. The multilayer composite tubular structure according to claim 1, wherein the inner layer is stainless steel.

4. The multilayer composite tubular structure according to claim 1, wherein the middle layer is selected from the group consisting of tantalum, gold, gold alloy, platinum, and platinum alloy.

5. The multilayer composite tubular structure according to claim 1, wherein the thickness of the radiopaque layer is selected to produce a luminosity on a fluoroscope.

6. A multilayer composite tubular structure for use as a stent in surgical procedures, comprising:
   (a) an outer tube of biocompatible material;
   (b) an inner tube of biocompatible material, the inner tube having a layer of radiopaque material deposited on the outer surface thereof, the radiopaque layer being metallurgically bonded to the outer tube.

7. The multilayer composite tubular structure according to claim 6, wherein the radiopaque material is deposited on the outer surface of the inner tube through a process selected from the group consisting of vapor deposition, electroplating, and spraying.

8. The multilayer composite tubular structure according to claim 6, wherein the outer tube is formed from stainless steel.

9. The multilayer composite tubular structure according to claim 6, wherein the inner tube is formed from stainless steel.

10. The multilayer composite tubular structure according to claim 6, wherein the radiopaque layer is selected from the group consisting of tantalum, gold, gold alloy, platinum, and platinum alloy.

11. The multilayer composite tubular structure according to claim 6, wherein the thickness of the radiopaque layer is selected to produce a luminosity on a fluoroscope.

12. A multilayer composite tubular structure for use as a stent in surgical procedures, comprising:
   (a) an outer tube of biocompatible material, the outer tube having a layer of radiopaque material deposited on the inner surface thereof;
   (b) an inner tube of biocompatible material, the radiopaque layer being metallurgically bonded to the inner tube.

13. The multilayer composite tubular structure according to claim 12, wherein the radiopaque material is deposited on the inner surface of the outer tube through selected from the group consisting of vapor deposition, electroplating, and spraying.

14. The multilayer composite tubular structure according to claim 12, wherein the outer tube is formed from stainless steel.

15. The multilayer composite tubular structure according to claim 12, wherein the inner tube is formed from stainless steel.

16. The multilayer composite tubular structure according to claim 12, wherein the radiopaque layer selected from the group consisting of tantalum, gold, gold alloy, platinum, and platinum alloy.

17. The multilayer composite tubular structure according to claim 12, wherein the thickness of the radiopaque layer is selected to produce a luminosity on a fluoroscope.

18. A multilayer composite tubular structure for use as a stent in surgical procedures, comprising a layer of radiopaque metallic material and a layer of biocompatible metallic material, each layer being metallurgically bonded to a suitable metallic interleaf between the radiopaque material and the biocompatible material.

19. The multilayer composite tubular structure according to claim 18, wherein the metallic interleaf is formed from gold.

20. The multilayer composite tubular structure according to claim 18, wherein the thickness of the radiopaque layer is selected to produce a luminosity on a fluoroscope.

21. The process of forming a multilayer composite tubular structure for use as a stent in surgical procedures, comprising:
   (a) surrounding a tube of radiopaque material coaxially with a tube of biocompatible material;
   (b) reducing the tubes simultaneously to a desired diameter and thereby producing a residual clamping stress between the tubes;
   (c) heat treating the tubes to cause diffusion bonding of the tubes so that the composite tube formed is ductile and will permit deformation without delamination between the radiopaque and biocompatible materials.

22. The process of forming a multilayer composite tubular structure according to claim 21, wherein the layers are reduced by one of the steps of tube drawing and swaging.

23. The process of forming a multilayer composite tubular structure according to claim 21, wherein the residual clamping stress is at least 50 p.s.i.

24. The process of forming a multilayer composite tubular structure according to claim 21, wherein heat is applied in step (c) at a temperature of at least 1550° F.

25. The process of forming a multilayer composite tubular structure according to claim 21, wherein heat is applied in step (c) at a temperature not greater than 1850° F.

26. The process of forming a multilayer composite tubular structure according to claim 21, wherein heat is applied in step (c) for between 6 and 15 minutes.

27. The process of forming a multilayer composite tubular structure according to claim 21, wherein heat is applied in step (c) in the temperature range from about 1550° F. to about 1850° F. for between 6 to 15 minutes.

28. A process of forming a multilayer composite tubular structure for use as a stent in surgical procedures, comprising:

(a) depositing a radiopaque layer onto the outer surface of a first tube, the first tube formed from biocompatible material;
(b) coaxially surrounding the first tube with a second tube formed from biocompatible material;
(c) reducing the tubes simultaneously to a desired diameter and thereby producing a residual clamping stress between the tubes;
(d) heat treating the tubes to cause diffusion bonding of the radiopaque layer to the outer tube, to form a composite tube which is ductile and will permit deformation without delamination between the radiopaque and biocompatible materials.

29. The process of forming a multilayer composite tubular structure according to claim 28, wherein the radiopaque material is deposited on the outer surface of the first tube through a process selected from the group consisting of vapor deposition, electroplating, and spraying.

30. The process of forming a multilayer composite tubular structure according to claim 28, wherein the tubes are reduced by one of the steps of tube drawing and swaging.

31. The process of forming a multilayer composite tubular structure according to claim 28, wherein the residual clamping stress is at least 50 p.s.i.

32. The process of forming a multilayer composite tubular structure according to claim 28, wherein heat is applied in step (d) at a temperature of at least 1550° F.

33. The process of forming a multilayer composite tubular structure according to claim 28, wherein heat is applied in step (d) at a temperature not greater than 1850° F.

34. The process of forming a multilayer composite tubular structure according to claim 28, wherein heat is applied in step (d) for between 6 and 15 minutes.

35. The process of forming a multilayer composite tubular structure according to claim 28, wherein heat is applied in step (d) in the temperature range from about 1550° F. to about 1850° F. for between 6 to 15 minutes.

36. A process for forming a multilayer composite tubular structure for use as a stent in surgical procedures, comprising:
(a) depositing a radiopaque layer onto the inner surface of a first tube of biocompatible material;
(b) placing the first tube coaxially around a second tube of biocompatible material;
(c) reducing the tubes simultaneously to a desired diameter and thereby producing a residual clamping stress between the tubes;
(d) heat treating the tubes to cause diffusion bonding of the radiopaque layer and the inner surface of the outer tube, wherein the composite tube formed is ductile and will permit deformation without delamination between the radiopaque and biocompatible materials.

37. The process of forming a multilayer composite tubular structure according to claim 36, wherein the radiopaque material is deposited on the inner surface of the first tube through a process selected from the group consisting of vapor deposition, electroplating, and spraying.

38. The process of forming a multilayer composite tubular structure according to claim 36, wherein the tubes are reduced by one of the steps of tube drawing and swaging.

39. The process of forming a multilayer composite tubular structure according to claim 36, wherein the residual clamping stress is at least 50 p.s.i.

40. The process of forming a multilayer composite tubular structure according to claim 36, wherein heat is applied in step (d) at a temperature of at least 1550° F.

41. The process of forming a multilayer composite tubular structure according to claim 36, wherein heat is applied in step (d) at a temperature not greater than 1850° F.

42. The process of forming a multilayer composite tubular structure according to claim 36, wherein heat is applied in step (d) for between 6 and 15 minutes.

43. The process of forming a multilayer composite tubular structure according to claim 36, wherein heat is applied in step (d) in the temperature range from about 1550° F. to about 1850° F. for between 6 to 15 minutes.

44. A process of forming a multilayer composite tubular structure for use as a stent in surgical procedures, comprising:
(a) surrounding a tube of radiopaque material coaxially with a tube of biocompatible material;
(b) placing a metallic interleaf between the radiopaque and biocompatible tubes;
(c) reducing the tubes simultaneously to a desired diameter and thereby producing a residual clamping stress between the tubes;
(d) heat treating the tubes to cause diffusion bonding of the radiopaque layer and the biocompatible layer so that the composite tube formed is ductile and will permit deformation without delamination.

45. The process of forming a multilayer composite tubular structure according to claim 44, wherein the layers are reduced by one of the steps of tube drawing and swaging.

46. The process of forming a multilayer composite tubular structure according to claim 44, wherein the residual clamping stress is at least 50 p.s.i.

47. The process of forming a multilayer composite tubular structure according to claim 44, wherein heat is applied in step (d) at a temperature of a least 1550° F.

48. The process of forming a multilayer composite tubular structure according to claim 44, wherein heat applied is applied in step (d) at a temperature not greater than 1850° F.

49. The process of forming a multilayer composite tubular structure according to claim 44, wherein heat is applied in step (d) for between 6 and 15 minutes.

50. The process of forming a multilayer composite tubular structure according to claim 44, wherein heat is applied in step (d) in the temperature range from about 1550° F. to about 1850° F. for between 6 to 15 minutes.

51. A process for forming a multilayer composite tubular structure for use as a stent in surgical procedures, comprising:
(a) placing a strip having a layer of radiopaque material and a layer of biocompatible material over a die;
(b) reducing the strip by deep drawing the strip through a series of dies, thereby producing a clamping stress between the layers and forming a tube of desired wall thickness having a closed end;
(c) removing the closed end of the tube once the desired wall thickness has been achieved; and
(d) heat treating the tube to cause diffusion bonding of the radiopaque layer and the biocompatible layers so that the composite tube formed is ductile and will permit deformation without delamination between the radiopaque and biocompatible layers.

52. The process of forming a multilayer composite tubular structure according to claim 51, wherein the residual clamping stress is at least 50 p.s.i.

53. The process of forming a multilayer composite tubular structure according to claim 51, wherein heat is applied in step (d) at a temperature of at least 1550° F.

54. The process of forming a multilayer composite tubular structure according to claim 51, wherein heat is applied in step (d) at a temperature not greater than 1850° F.

55. The process of forming a multilayer composite tubular structure according to claim 51, wherein heat is applied in step (d) for between 6 and 15 minutes.

56. The process of forming a multilayer composite tubular structure according to claim 51, wherein heat is applied in step (d) in the temperature range from about 1550° F. to about 1850° F. for between 6 to 15 minutes.

57. A process of delivering a multilayer composite metallic tubular structure for use as a surgical stent to an anatomical site, comprising:

(a) providing a metallic tubular structure having metallurgically bonded metal biocompatible and radiopaque layers;

(b) deploying the structure to an anatomical site;

(c) expanding the structure with a balloon using a pressure not greater than 3.5 atmospheres until the walls of the structure contact tissue at the anatomical site; and (d) imbedding the structure into said tissue at the anatomical site by further expanding the structure with a balloon using a pressure not greater than 7.5 atmospheres.

* * * * *